United States Patent
Lawler et al.

(10) Patent No.: US 10,125,185 B2
(45) Date of Patent: Nov. 13, 2018

(54) THROMBOSPONDIN-1 POLYPEPTIDES AND METHODS OF USING SAME

(71) Applicants: Beth Israel Deaconess Medical Center, Inc., Boston, MA (US); University of Guelph, Guelph (CA)

(72) Inventors: John W. Lawler, Swampscott, MA (US); Mark Duquette, Southborough, MA (US); James Petrik, Rockwood (CA)

(73) Assignees: Beth Israel Deaconess Medical Center, Inc., Boston, MA (US); University of Guelph, Guelph (CA)

( * ) Notice: Subject to any disclaimer, the term of this patent is extended or adjusted under 35 U.S.C. 154(b) by 0 days.

(21) Appl. No.: 15/057,923

(22) Filed: Mar. 1, 2016

(65) Prior Publication Data

US 2016/0176948 A1    Jun. 23, 2016

Related U.S. Application Data

(62) Division of application No. 14/204,110, filed on Mar. 11, 2014.

(60) Provisional application No. 61/782,136, filed on Mar. 14, 2013.

(51) Int. Cl.
*C07K 14/78* (2006.01)
*C07K 16/00* (2006.01)
*A61K 47/68* (2017.01)

(52) U.S. Cl.
CPC .............. *C07K 14/78* (2013.01); *A61K 47/68* (2017.08); *C07K 16/00* (2013.01); *C07K 2319/30* (2013.01)

(58) Field of Classification Search
None
See application file for complete search history.

(56) References Cited

U.S. PATENT DOCUMENTS

| 7,223,731 | B2 | 5/2007 | Lawler |
| 2004/0110131 | A1 | 6/2004 | Lawler |
| 2007/0041967 | A1* | 2/2007 | Jung ...................... C07K 19/00 424/133.1 |

FOREIGN PATENT DOCUMENTS

| WO | WO-01/91781 A2 | 12/2001 |
| WO | WO-02/060919 A2 | 8/2002 |

OTHER PUBLICATIONS

Alvarez et al., "Thrombospondin-1 expression in epithelial ovarian carcinoma: association with p53 status, tumor angiogenesis, and survival in platinum-treated patients," Gynecol Oncol. 82(2):273-8 (2001).

Asch et al., "Thrombospondin sequence motif (CSVTCG) is responsible for CD36 binding," Biochem Biophys Res Commun. 182(3):1208-17 (1992).

Campbell et al., "Molecular mediators of angiogenesis in bladder cancer," Cancer Res. 58(6):1298-304 (1998).

Dall'Acqua et al., "Properties of human IgG1s engineered for enhanced binding to the neonatal Fc receptor (FcRn)," J Biol Chem. 281(33):23514-24 (2006).

Dawson et al., "CD36 mediates the in vitro inhibitory effects of thrombospondin-1 on endothelial cells," J Cell Biol. 138(3): 707-17 (1997).

Dawson et al., "Three distinct D-amino acid substitutions confer potent antiangiogenic activity on an inactive peptide derived from a thrombospondin-1 type 1 repeat," Mol Pharmacol. 55(2):332-8 (1999).

Ebbinghaus et al., "Phase 2 study of ABT-510 in patients with previously untreated advanced renal cell carcinoma," Clin Cancer Res. 13(22 Pt 1):6689-95 (2007).

Greenaway et al., "ABT-510 induces tumor cell apoptosis and inhibits ovarian tumor growth in an orthotopic, syngeneic model of epithelial ovarian cancer," Mol Cancer Ther. 8(1):64-74 (2009) (20 pages).

Greenaway et al., "Thrombospondin-1 inhibits VEGF levels in the ovary directly by binding and internalization via the low density lipoprotein receptor-related protein-1 (LRP-1)," J Cell Physiol. 210(3):807-18 (2007) (24 pages).

Hsu et al., "Inhibition of angiogenesis in human glioblastomas by chromosome 10 induction of thrombospondin-1," Cancer Res. 56(24):5684-91 (1996).

Huang et al., "Peroxisome proliferator-activated receptor gamma ligands improve the antitumor efficacy of thrombospondin peptide ABT510," Mol Cancer Res. 2(10):541-50 (2004).

Iruela-Arispe et al., "Inhibition of angiogenesis by thrombospondin-1 is mediated by 2 independent regions within the type 1 repeats," Circulation. 100(13):1423-31 (1999).

Jiménez et al., "c-Jun N-terminal kinase activation is required for the inhibition of neovascularization by thrombospondin-1," Oncogene. 20(26):3443-8 (2001).

Jiménez et al., "Signals leading to apoptosis-dependent inhibition of neovascularization by thrombospondin-1," Nat Med. 6(1):41-8 (2000).

Kazerounian et al., "Priming of the vascular endothelial growth factor signaling pathway by thrombospondin-1, CD36, and spleen tyrosine kinase," Blood. 117(17):4658-66 (2011).

Kerbel et al., "Clinical translation of angiogenesis inhibitors," Nat Rev Cancer. 2(10):727-39 (2002).

Lawler, "Thrombospondin-1 as an endogenous inhibitor of angiogenesis and tumor growth," J Cell Mol Med. 6(1):1-12 (2002).

Li et al., "Antitumor efficacy of a thrombospondin 1 mimetic CovX-body," Transl Oncol. 4(4):239-47 (2011).

(Continued)

*Primary Examiner* — Nelson B Moseley, II
(74) *Attorney, Agent, or Firm* — Clark & Elbing LLP

(57) ABSTRACT

The invention features thrombospondin-1 (TSP-1) polypeptides (e.g., 3TSR-Fc fusion proteins), nucleic acid molecules encoding the TSP-1 polypeptides, and compositions thereof. The invention also features methods of making and using the TSP-1 polypeptides of the invention (e.g., using 3TSR-Fc fusion proteins to treat a subject having a disorder associated with pathological angiogenesis, e.g., cancer, e.g., epithelial ovarian cancer (EOC)).

24 Claims, 6 Drawing Sheets
(3 of 6 Drawing Sheet(s) Filed in Color)
Specification includes a Sequence Listing.

(56) References Cited

OTHER PUBLICATIONS

Miao et al., "Thrombospondin-1 type 1 repeat recombinant proteins inhibit tumor growth through transforming growth factor-beta-dependent and -independent mechanisms," Cancer Res. 61(21):7830-9 (2001).

Petrik et al., "Expression and localization of thrombospondin-1 and -2 and their cell-surface receptor, CD36, during rat follicular development and formation of the corpus luteum," Biol Reprod. 67(5):1522-31 (2002).

Reiher et al., "Inhibition of tumor growth by systemic treatment with thrombospondin-1 peptide mimetics," Int J Cancer. 98(5):682-9 (2002).

Ren et al., "A double hit to kill tumor and endothelial cells by TRAIL and antiangiogenic 3TSR," Cancer Res. 69(9):3856-65 (2009) (19 pages).

Ren et al., "Regulation of tumor angiogenesis by thrombospondin-1," Biochim Biophys Acta. 1765(2):178-88 (2006).

Russell et al., "Combined therapy with thrombospondin-1 type I repeats (3TSR) and chemotherapy induces regression and significantly improves survival in a preclinical model of advanced stage epithelial ovarian cancer," FASEB J. 29(2):576-88 (2015).

Tan et al., "Crystal structure of the TSP-1 type 1 repeats: a novel layered fold and its biological implication," J Cell Biol. 159(2):373-82 (2002).

Tolsma et al., "Peptides derived from two separate domains of the matrix protein thrombospondin-1 have anti-angiogenic activity," J Cell Biol. 122(2):497-511 (1993).

Volpert et al., "Inducer-stimulated Fas targets activated endothelium for destruction by anti-angiogenic thrombospondin-1 and pigment epithelium-derived factor," Nat Med. 8(4):349-57 (2002).

Westphal, "Technology evaluation: ABT-510, Abbott," Curr Opin Mol Ther. 6(4):451-7 (2004).

Zhang et al., "Thrombospondin-1 modulates vascular endothelial growth factor activity at the receptor level," FASEB J. 23(10):3368-76 (2009).

* cited by examiner

Figures 2A-2B
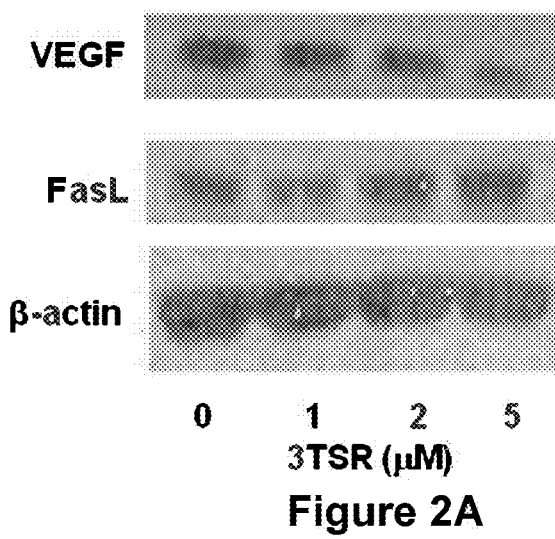
Figure 2A
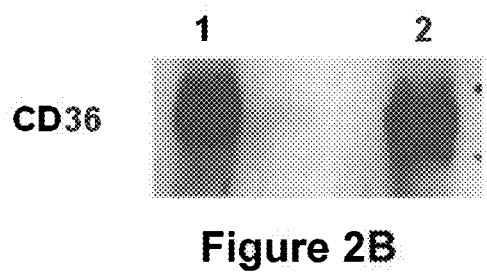
Figure 2B

THROMBOSPONDIN-1 POLYPEPTIDES AND METHODS OF USING SAME

CROSS-REFERENCE TO RELATED APPLICATIONS APPLICATION

This application is a divisional application of U.S. patent application Ser. No. 14/204,110, filed Mar. 11, 2014, which claims the benefit of the filing date of U.S. Provisional Application No. 61/782,136, filed Mar. 14, 2013, each of which is hereby incorporated by reference.

STATEMENT AS TO FEDERALLY FUNDED RESEARCH

This invention was made with government support under Grant No. CA130895, awarded by the National Institutes of Health (NIH). The government has certain rights in the invention.

BACKGROUND OF THE INVENTION

Thrombospondin-1 (TSP-1) is a potent endogenous inhibitor of tumor growth and angiogenesis. It inhibits endothelial cell growth, migration, and tube formation in vitro. In vitro assays have shown that platelet TSP-1 is involved in thrombosis, fibrinolysis, wound healing, inflammation, tumor cell metastasis, and angiogenesis. TSP-1 is the major form of thrombospondin secreted by platelets and endothelial cells.

The in-growth of new capillary networks into developing tumors is essential for the progression of cancer, such as epithelial ovarian cancer (EOC). EOC is the leading cause of death from gynaecological malignancy and the fifth most common cause of cancer-related death in women. In 2013, it is estimated that 22,240 new ovarian cancer cases will be diagnosed in the United States and that 14,030 will succumb to the disease (*American Cancer Society: Cancer Facts and Figures* 2013. Atlanta, Ga., 2013). The poor ratio of survival to incidence in EOC is related to the high percentage of cases that are diagnosed at an advanced stage and the lack of effective therapies for advanced refractory disease. Despite improvements in surgical techniques, survival of patients with EOC stands at 45% at five years (Jemal et al. *Cancer Statistics*. 58: 71-96, 2008).

Thus, there is an unmet need in the field for the development of novel anti-angiogenic therapies for effectively treating cancer, such as EOC, to allow for more successful treatment outcomes.

SUMMARY OF THE INVENTION

In a first aspect, the invention features a polypeptide including a thrombospondin-1 (TSP-1) domain, or portion thereof, and a fragment crystallizable (Fc) region.

In some embodiments, the TSP-1 domain, or portion thereof, is a type 1 repeat (TSR) domain, or portion thereof. In some embodiments, the TSR domain, or portion thereof, is a TSR domain, or portion thereof, of human TSP-1. The TSR domain, or portion thereof, of human TSP-1 may include the first type 1 repeat (TSR1) of TSP-1 (amino acid residues 360-416) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 1 (TSR1) or SEQ ID NO: 2 (TSR1(R413Q)); the second type 1 repeat (TSR2) of TSP-1 (amino acid residues 417-473) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 3 (TSR2+RFK) or SEQ ID NO: 4 (TSR2); or the third type 1 repeat (TSR3) of TSP-1 (amino acid residues 474-530) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 5 (TSR3). In some embodiments, the TSR domain, or portion thereof, of human TSP-1 may include all three TSRs (TSR1, TSR2, and TSR3) of TSP-1 (amino acids 360-530) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 6 (3TSR (R413Q)) or SEQ ID NO: 7 (3TSR). In other embodiments, the TSR domain, or portion thereof, of human TSP-1 may include a combination of two different TSRs (e.g., TSR1 and TSR2; TSR2 and TSR3; or TSR1 and TSR3). In yet other embodiments, the amino acid sequence of the TSR domain, or portion thereof, of human TSP-1 consists of any one of SEQ ID NOs: 1-7.

In some embodiments, the Fc region includes a CH2 domain and a CH3 domain. The Fc region may further include a hinge region. In some embodiments, the CH2 domain and the CH3 domain are heavy chain constant domains of an immunoglobulin selected from the group consisting of IgG1, IgG2, IgG3, and IgG4. In particular embodiments, the immunoglobulin is IgG1. In other particular embodiments, the Fc region includes an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO: 8. For example, the amino acid sequence of the Fc region optionally includes SEQ ID NO: 8 or consists of SEQ ID NO: 8.

In some embodiments, the TSP-1 domain, or portion thereof, and the Fc region are positioned relative to each other in an N-terminal to C-terminal direction as follows: X-TSP-1 domain-Y-Fc region-Z. In other embodiments, the TSP-1 domain, or portion thereof, and the Fc region are positioned relative to each other in an N-terminal to C-terminal direction as follows: X-Fc region-Y-TSP-1 domain-Z. In either of the two above embodiments, each of X, Y, and Z is absent or is an amino acid sequence of at least one amino acid (e.g., at least 2, 3, 4, 5, 6, 7, 8, 9, 10, 15, 20, 25, 30, 35, 40, 45, or 50 or more amino acids). The polypeptide may further include a linker or spacer region positioned between the TSP-1 domain, or portion thereof, and the Fc region (e.g., when Y is at least one amino acid). In yet other embodiments, the Fc region is conjugated to a functional moiety.

In a second aspect, the invention features a polynucleotide encoding one or more polypeptides of the first aspect. One or more polynucleotides of the second aspect may optionally be included in a vector (e.g., a recombinant expression vector).

In a third aspect, the invention features a host cell including one or more polynucleotides and/or vectors of the second aspect. In some embodiments, the host cell is a mammalian cell (e.g., CHO, HeLa, 3T3, BHK, COS, 293, and Jurkat cells). In other embodiments, the host cell is a prokaryotic cell (e.g., an *E. coli* cell).

In a fourth aspect, the invention features a method of producing a polypeptide of the first aspect that includes culturing a host cell of the third aspect in a culture medium. In some embodiments, the method further includes recovering the polypeptide from the host cell or the culture medium. In some embodiments, the method is performed in vitro or ex vivo.

In a fifth aspect, the invention features a composition including a polypeptide of the first aspect and/or a polynucleotide of the second aspect. In some embodiments, the composition further includes a pharmaceutically acceptable carrier, excipient, or diluent. The composition may optionally include an adjuvant. In other embodiments, the composition is formulated for treating a disorder associated with pathological angiogenesis (e.g., cancer, e.g., ovarian cancer, e.g., epithelial ovarian cancer (EOC)) in a subject (e.g., a mammal, e.g., a human, e.g., a woman).

In a sixth aspect, the invention features a method of treating a subject having a disorder associated with pathological angiogenesis (e.g., EOC) including administering a therapeutically effective amount of a composition of the fifth aspect to the subject, thereby treating the subject. In some embodiments, the composition is administered to the subject in a dosage of about 0.01 mg/kg/wk to about 10 mg/kg/wk. For example, the composition may be administered to the subject in a dosage of about 0.1 mg/kg/wk to about 1 mg/kg/wk.

In a seventh aspect, the invention features a method of treating a subject having a disorder associated with pathological angiogenesis (e.g., EOC) including administering a therapeutically effective amount of a composition that includes a TSR-containing polypeptide including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 1-7 or a polynucleotide encoding the polypeptide. In some embodiments, the polypeptide is not full-length thrombospondin-1 (TSP-1) and the polynucleotide does not encode full-length TSP-1. In some embodiments, the polypeptide consists of any one of SEQ ID NOs: 1-7. In other embodiments, the composition is administered to said subject in a dosage of about 0.5 mg/kg/day to about 10 mg/kg/day.

In any embodiment of the sixth or seventh aspect, the disorder may be cancer. The cancer may be ovarian cancer, such as epithelial ovarian cancer (EOC). The EOC may be Stage III EOC or Stage IV EOC.

In any embodiment of the sixth or seventh aspect, the size of primary tumors in the subject may be reduced after administration of the composition to the subject; the presence of metastatic peritoneal tumors and ascites in the subject may be reduced after administration of the composition to the subject; apoptosis of EOC cells in the subject is induced after administration of the composition to the subject; and/or a lack of progression of EOC results after administration of said composition to said subject.

In some embodiments, the composition is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. In some embodiments, the composition may be administered by localized drug delivery. In some embodiments, the localized drug delivery system results in the slow release of the composition. In some embodiments, the subject is administered at least one dose (e.g., 1, 2, 3, 4, 5, 6, 7, 8, 9, 10, or more doses) of the composition or is administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. In other embodiments, the subject is administered at least two doses (e.g., 2, 3, 4, 5, 6, 7, 8, 9, 10, or more doses) of the composition. In yet other embodiments, the composition is administered to the subject between one and seven times a week. When treating disorder associated with pathological angiogenesis (e.g., EOC), the composition(s) of the fifth aspect of the invention may be administered to the subject either before the occurrence of symptoms of disorder associated with pathological angiogenesis (e.g., EOC) or a definitive diagnosis, or after diagnosis or symptoms become evident. The composition(s) may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In a final aspect, the invention features a kit including: (a) a composition of the fifth aspect of the invention; and (b) instructions for administering the composition to a subject to treat a disorder associated with pathological angiogenesis (e.g., EOC). The kit may optionally include an adjuvant.

In preferred embodiments of all aspects of the invention, the subject is a mammal, preferably a human, such as a woman.

Definitions

As used herein, the term "about" means +/−10% of the recited value.

As used herein, "administering" is meant a method of giving a dosage of a composition (e.g., a composition of the fifth aspect) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The preferred method of administration can vary depending on various factors (e.g., the components of the composition being administered and the severity of the condition, disease, or disorder being treated).

A "disorder associated with pathological angiogenesis" is any condition that is characterized by new blood vessels growing excessively, insufficiently, or inappropriately (e.g., the location, timing or onset of the angiogenesis being undesired from a medical standpoint) in a diseased state or such that it causes a diseased state, which would benefit from treatment with a thrombospondin-1 (TSP-1) polypeptide (e.g., a polypeptide including a TSP-1 domain or portion thereof, e.g., a 3TSR-Fc fusion protein) or composition including a polypeptide including a TSP-1 domain or portion thereof. Non-limiting examples of disorders to be treated herein include cancers, such as ovarian cancer, such as epithelial ovarian cancer (EOC), and related diseases or disorders.

Excessive, inappropriate, or uncontrolled angiogenesis occurs when there is new blood vessel growth that contributes to the worsening of the diseased state or causes a diseased state, such as in cancer, especially vascularized solid tumors and metastatic tumors. The new blood vessels can feed the diseased tissues, destroy normal tissues, and in the case of cancer, the new vessels can allow tumor cells to escape into the circulation and lodge in other organs (tumor metastases). Insufficient angiogenesis occurs when there is inadequate blood vessel growth that contributes to the worsening of a diseased state, for example, in diseases such as coronary artery disease, stroke, and delayed wound healing. Further, ulcers, strokes, and heart attacks can result from the absence of angiogenesis that is normally required for natural healing. The present invention contemplates treating those patients that are at risk of developing the above-mentioned illnesses.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. A more particular example of such cancer is ovarian cancer, such as epithelial ovarian cancer (EOC).

By "composition" is meant a composition containing a polypeptide or nucleic acid described herein, optionally formulated with a pharmaceutically acceptable carrier, excipient, or diluent, and manufactured or sold with the approval of a governmental regulatory agency as part of a therapeutic regimen for the treatment of disease or disorder (e.g., a disorder associated with pathological angiogenesis, e.g., epithelial ovarian cancer (EOC)) in a mammal (e.g., a human, e.g., a woman). Compositions can be formulated, for example, for administration via a localized drug delivery (e.g., a localized slow-release drug delivery system); for oral administration in unit dosage form (e.g., a tablet, capsule, caplet, gelcap, or syrup); for intravenous administration (e.g., as a sterile solution free of particulate emboli and in a solvent system suitable for intravenous use); for subcutaneous administration; or any other formulation described herein.

Throughout this specification and claims, the word "comprise," or variations such as "comprises" or "comprising," will be understood to imply the inclusion of a stated integer or group of integers but not the exclusion of any other integer or group of integers.

The "EU numbering system" or "EU index" is generally used when referring to a residue in an immunoglobulin heavy chain constant region (e.g., the EU index reported in Kabat et al., Sequences of Immunological Interest. 5th Ed. Public Health Service, National Institutes of Health, Bethesda, Md. (1991)). The "EU index as in Kabat" refers to the residue numbering of the human IgG1 EU antibody. Unless stated otherwise herein, references to residue numbers in the heavy chain constant domain of antibodies (e.g., CH1, CH2, or CH3 domains) means residue numbering by the EU numbering system.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton. *Molec. Immunol.* 22: 161-206, 1985).

The "CH3 domain" comprises the stretch of residues C-terminal to a CH2 domain in an Fc region (i.e., from about amino acid residue 341 to about amino acid residue 447 of an IgG).

The term "Fc region," or "fragment crystallizable region," herein is used to define a C-terminal region of an immunoglobulin (e.g., an IgG1, IgG2, IgG3, or IgG4) heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region may be engineered to include one or more mutations (e.g., M252Y, S254T, T256E, H433K, and/or N434F) that increase the half-life of the Fc region and any fused polypeptide (e.g., a TSP-1 domain, or portion thereof) or non-polypeptide (e.g., a non-polypeptide functional moiety) component in circulation. The C-terminal lysine (residue 447 according to the EU numbering system) of the Fc region may be removed, for example, during production or purification of the antibody, or by recombinantly engineering the nucleic acid encoding a heavy chain of the antibody. The Fc region may also include any portion of a hinge region (e.g., a native or modified hinge region). The Fc can be of any mammal, including human, and may be post-translationally modified (e.g., by glycosylation). In a non-limiting example, the Fc region can be of human IgG1 having the amino acid sequence of SEQ ID NO: 8.

By "functional moiety" is meant a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARTNOL®); beta-lapachone;

lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem. Intl. Ed. Engl. 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, EL), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® GnRH antagonist; lapatinib ditosylate (an ErbB-2 and EGFR dual tyrosine kinase small-molecule inhibitor also known as GW572016); and pharmaceutically acceptable salts, acids or derivatives of any of the above.

"Hinge region" is generally defined as stretching from Glu216 to Pro230 of human IgG1 (Burton. *Molec. Immunol.* 22: 161-206, 1985). Hinge regions of other IgG isotypes may be aligned with the IgG1 sequence by placing the first and last cysteine residues forming inter-heavy chain S—S bonds in the same positions.

By "induce," or variations such as "induced" or "induces" or "inducing," with respect to apoptosis of epithelial ovarian cancer (EOC) cells refers to an increase in apoptosis of EOC cells by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more in a treated subject (e.g., according to the methods of the sixth and/or seventh aspects of the invention) compared to that of a control subject (e.g., an untreated subject or a subject treated with a placebo).

By "pharmaceutically acceptable carrier, excipient, or diluent" is meant a carrier, excipient, or diluent which is physiologically acceptable to the subject while retaining the therapeutic properties of the composition with which it is administered. One exemplary pharmaceutically acceptable carrier is physiological saline. Other physiologically acceptable excipients and their formulations are known to one skilled in the art and described, for example, in "Remington: The Science and Practice of Pharmacy" (20th ed., ed. A. R. Gennaro, 2000, Lippincott Williams & Wilkins).

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

By "polypeptide" or "protein" is meant any natural or synthetic chain of amino acids at least two amino acids (e.g., 5, 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 700, 800, or more amino acids) in length, including those having post-translational modification (e.g, glycosylation or phosphorylation).

By "portion" or "fragment" is meant a part of a whole. A portion may comprise at least 10%, 20%, 30%, 40%, 50%, 60%, 70%, 80%, 90%, or 95% of the entire length of an polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 2000, or more contiguous nucleotides of a reference polynucleotide molecule. For polypeptides, for example, a portion may include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, 350, 400, 450, 500, 550, 600, 650, 700, 750 or more contiguous amino acids of a reference polypeptide molecule.

As used herein, the term "reduce," or variations such as "reduced" or "reduces" or "reducing," with respect to the size of primary tumors and the presence of metastatic peritoneal tumors and ascites, refers to a decrease in primary tumor size and in the presence or number of metastatic peritoneal tumors and ascites, respectively, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more in a treated subject (e.g., according to the methods of the sixth and/or seventh aspects of the invention) compared to that of a control subject (e.g., an untreated subject or a subject treated with a placebo).

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al. *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, 800 or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, 2200, 2300, 2400 or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By amino acid "spacer" or "linker" as used herein is meant an amino acid sequence of two or more amino acids in length that is not cleavable, for example, by auto-cleavage, enzymatic, or chemical cleavage. The spacer can consist of neutral, polar, or nonpolar amino acids. In preferred embodiments, the spacer or linker is positioned between a thrombospondin-1 (TSP-1) domain, or fragment thereof, (e.g., 3TSR) and a fragment crystallizable (Fc) region. An amino acid spacer can be, for example, 2 to 100 amino acids in length, for example, 3, 5, 10, 15, 20, 25, 30, 35, 40, 45, 50, 55, 60, 65, 70, 75, 80, 85, 90, or 95 amino acids in length.

A "subject" is a vertebrate, such as a mammal (e.g., a human, e.g., a woman). Mammals also include, but are not limited to, farm animals (such as cows), sport animals (e.g., horses), pets (such as cats and dogs), mice, and rats. A subject to be treated according to the methods described herein (e.g., a subject having a disorder associated with pathological angiogenesis, e.g., cancer, e.g., epithelial ovarian cancer (EOC)) may be one who has been diagnosed by a medical practitioner as having such a condition. Diagnosis may be performed by any suitable means. One skilled in the art will understand that a subject to be treated according to the present invention may have been subjected to standard tests or may have been identified, without examination, as one at high risk due to the presence of one or more risk factors (e.g., a family history of ovarian cancer, breast cancer, and/or colorectal cancer; age greater than 40 years (e.g., age greater than 63 years); body mass index (BMI) ≥30; no tubal ligation; and/or use of androgens and/or estrogens).

By "therapeutically effective amount" is meant an amount of a therapeutic agent that alone, or together with one or more additional (optional) therapeutic agents, produces beneficial or desired results upon administration to a subject (e.g., a human, e.g., a woman). The therapeutically effective amount depends upon the context in which the therapeutic agent is applied. For example, in the context of administering a composition including a therapeutic agent such as a 3TSR-Fc fusion protein of the invention to a subject having EOC, the therapeutically effective amount of the composition is an amount sufficient to achieve a reduction in the size of primary tumors; and/or a reduction in the presence of metastatic peritoneal tumors and ascites; and/or an induction in apoptosis of EOC cells. Ideally, a therapeutically effective amount provides a therapeutic effect without causing a substantial cytotoxic effect in the subject. In general, a therapeutically effective amount of a composition administered to a subject (e.g., a human) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response.

By "thrombospondin-1 (TSP-1) domain" is meant any one of the defined structural domains of TSP-1 (i.e., amino-terminal domain, procollagen domain, type 1 repeat domain, type 2 repeat domain, type 3 repeat domain, and carboxyl-terminal domain), which, for example, for human TSP-1, may span amino acid residues 1-262 (amino-terminal domain), residues 263-359 (procollagen domain), residues 360-530 (type 1 repeat domain), residues 531-697 (type 2 repeat domain), residues 698-925 (type 3 repeat domain), and residues 926-1152 (carboxyl-terminal domain).

By "type 1 repeat" or "TSR" is meant any one of the three defined type 1 repeats (i.e., first type 1 repeat (TSR1), second type 1 repeat (TSR2), and third type 1 repeat (TSR3)) of the type 1 repeat domain of TSP-1, which, for example, for human TSP-1, may span amino acid residues 360-416 (TSR1), residues 417-473 (TSR2), and residues 474-530 (TSR3).

As used herein, and as well understood in the art, "treatment" or "treating" is meant an approach for obtaining beneficial or desired results, such as clinical results, which with respect to cancer, may include, for example, lack of progression or slowed progression of the cancer relative to one or more conventional or common therapies (e.g., chemotherapy, immunotherapy, hormonal therapy, radiation therapy, or surgery). Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, the term "vector" is meant to include, but is not limited to, naked DNA, oligonucleotides (e.g., plasmid), cationic lipid (e.g., liposome), cationic polymer (e.g., polysome), virosome, nanoparticle, dentrimer, or a virus (e.g., an viral vector, e.g., an adenovirus or poxvirus).

Other features and advantages of the invention will be apparent from the following Detailed Description, the drawings, and the claims.

BRIEF DESCRIPTION OF THE DRAWINGS

The application file contains at least one drawing executed in color. Copies of this patent or patent application with color drawings will be provided by the Office upon request and payment of the necessary fee.

FIG. 2A is a Western blot of whole cell lysates of 3TSR-treated ID8 cells probed for VEGF, Fas ligand (FasL), or β-actin (control), showing that FasL expression is increased and VEGF expression is decreased in a concentration-dependent manner upon treatment of 3TSR.

FIG. 2B is a Western blot of whole cell lysates of human dermal microvascular endothelial cells (HDMECs; lane 1) or ID8 cells (lane 2) probed for CD36, showing that the expression of CD36 in ID8 is comparable to that of HDMECs.

DETAILED DESCRIPTION OF THE INVENTION

Figure 1:
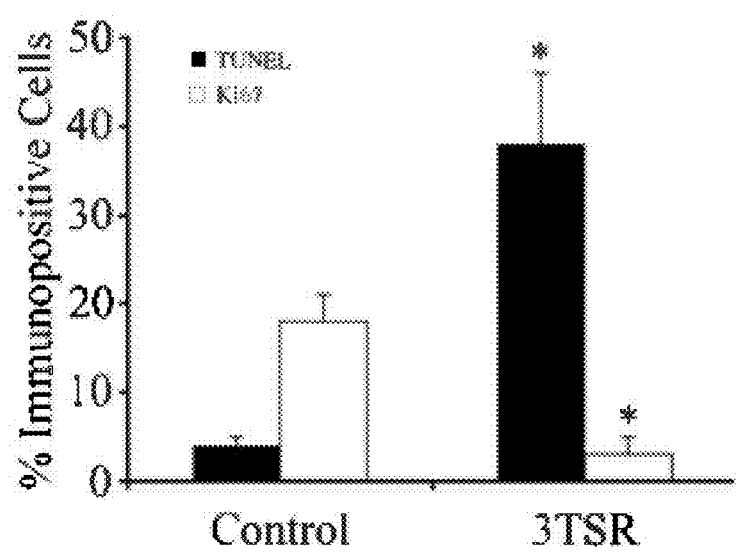
FIG. 1 is a graph showing that 3TSR treatment affects EOC cell proliferation and apoptosis in vitro. ID8 cells were cultured in presence or absence of 3TSR (3 µM) for 24 hours. 3TSR significantly (p<0.05) decreased the number of Ki67-positive proliferating cells (open bars) and increased the number of TUNEL-positive apoptotic cells (solid bars).

The present invention is based in part on the discovery of thrombospondin-1 (TSP-1) proteins (e.g., 3TSR) and fusions thereof (e.g., 3TSR-Fc fusion proteins) that are surprisingly efficacious in treating disorders associated with pathological angiogenesis, such as cancer (e.g., epithelial ovarian cancer (EOC)).

Thrombospondin-1 (TSP-1)

Thrombospondin-1 (TSP-1), also known as TSP, is a multimeric glycoprotein comprised of identical monomers. The monomers migrate at an apparent molecular weight of approximately 185 kDa in SDS-polyacrylamide electrophoretic gels under reducing conditions. The predominant multimer is a trimer, which migrates at an apparent molecular weight of approximately 450 kDa on non-reducing gels. The molecular weights by sedimentation equilibrium are similar, at 135 kDa for monomers and 420 kDa for trimers.

Thrombospondin-1 (TSP-1) has been shown to be an important negative regulator of tumor angiogenesis (Kerbel and Folkman. Nat. Rev. 107: 83-89, 2006). TSP-1 is a large extracellular matrix glycoprotein with potent antiangiogenic functions (Lawler. J. Cell Mol. Med. 6: 1-12, 2002). Reduced expression of TSP-1 is an important component of the angiogenic switch and its decrease facilitates growth of several tumor types including bladder, breast, and ovarian cancer, fibrosarcoma, and glioblastoma (Hsu et al. Cancer Res. 56: 5684-5691, 1996; Campbell et al. Cancer Res. 58: 1298-1304, 1998; Alvarez et al. Gynecol. Oncol 82: 273-278, 2001). TSP-1 inhibits angiogenesis by stimulating endothelial cell apoptosis and inhibiting endothelial cell migration (Jimenez et al. Nat. Med. 6: 4148, 2000) and by binding and sequestering proangiogenic growth factors such as VEGF (Greenaway et al. J. Cell Physiol. 210: 807-818, 2007). TSP-1 binds CD36, a receptor expressed on the surface of endothelial and steroidogenic cells in the ovary (Dawson et al. J. Cell Biol. 138: 707-717, 1997; Petrik et al. Biol. Reprod. 67: 1522-1531, 2002) as well as numerous other cell surface receptors such as integrin-associated protein/CD47, the low-density lipoprotein receptor-related protein-1, integrins, and various heparan sulfate proteoglycans (Ren et al. Biochim Biophys Acta. 765: 178-188, 2006). Through binding to this diverse array of receptors, TSP-1 has a multitude of functions in addition to inhibiting angiogenesis.

Significant progress has been made in our understanding of the molecular events that lead to the inhibition of angiogenesis by TSP-1, the first endogenous protein inhibitor of angiogenesis to be identified. The interaction of the type 1 repeats (TSRs) of TSP-1 with CD36 plays a significant role in the regulation of angiogenesis in vitro and in vivo (Jimenez et al. Nat Med. 6: 41-48, 2000; Dawson et al. Mol. Pharmacol. 55: 332-338, 1999; Dawson et al. J. Cell Biol. 138: 707-717, 1997). In vitro, CD36 mediates the inhibition of endothelial cell migration and tube formation by TSP-1 (Dawson et al. Mol. Pharmacol. 55: 332-338, 1999; Dawson et al. J. Cell Biol. 138: 707-717, 1997). Either GST fusion proteins containing the TSP-1-binding region of CD36 or antibodies against CD36 block the inhibition of endothelial cell migration caused by TSP-1. Transfection of CD36 into human umbilical vein endothelial cells (HUVECs) renders them more sensitive to inhibition of migration by TSP-1. Furthermore, molecules that bind CD36, including collagen, oxidized LDL, and an anti-CD36 IgM antibody, also inhibit endothelial cell migration (Dawson et al. J. Cell Biol. 138: 707-717, 1997). Whereas TSP-1 is a potent inhibitor of FGF-2-induced corneal neovascularization in wild-type mice, it is not active in CD36-null mice (Jimenez et al. Nat. Med. 6: 41-48, 2000). Jimenez et al. (Nat. Med. 6: 41-48, 2000) have shown that TSP-1 activation of a CD36-Fyn-caspase-3-p38 MAPK cascade is essential for TSP-1's anti-angiogenic effect, as well as its induction of endothelial cell apoptosis. Activation of this pathway leads to increased endothelial cell expression of Fas ligand, which sensitizes the cells to the increased levels of Fas that are induced by factors that initiate angiogenesis (Volpert et al. Nat. Med. 8: 349-357, 2002). This pathway may serve to limit the angiogenic response during physiological processes. The binding of TSP-1 or TSR-based peptides to CD36 also results in the transient activation of c-Jun N-terminal kinase (JNK) (Jimenez et al. Oncogene. 20: 3443-3448, 2001). We have found that induction of endothelial cell apoptosis by 3TSR involves activation of both caspase-8 and -9, and the up-regulation of death receptors (Ren et al. Cancer Res. 69: 3856-3865, 2009). We have made the surprising observation that 3TSR also antagonizes vascular endothelial cell growth factor receptor-2 (VEGFR-2) activation, suggesting that TSP-1 not only induces apoptosis, but also concomitantly suppresses pro-angiogenic signaling. Inhibition of VEGFR-2 activation may also inhibit endothelial cell migration in response to VEGF (Kazerounian et al. Blood. 117: 4658-4666, 2011; Zhang et al. FASEB J. 23: 3368-3376, 2009).

Although the native 450 kDa TSP-1 has been shown to have potent anti-angiogenic and anti-tumorigenic effects, its large size and complex functions limit the possibility of using it as a therapeutic anti-tumor strategy in humans. Therefore, here we investigated the anti-angiogenic and anti-tumorigenic effects of smaller TSP-1 proteins (e.g., a polypeptide including a TSP-1 domain or portion thereof, e.g., a 3TSR-Fc fusion polypeptide), as described in detail herein below.

TSP-1 Polypeptides

The invention features proteins, for example, fusion proteins, including a thrombospondin-1 (TSP-1) domain, or portion thereof, and optionally a fragment crystallizable (Fc) region. The TSP-1 domain, or portion thereof, may be a type 1 repeat (TSR) domain, or portion thereof. The TSR domain, or portion thereof, may be a TSR domain, or portion thereof, of human TSP-1. The TSR domain, or portion thereof, of human TSP-1 may include the first type 1 repeat (TSR1) of TSP-1 (amino acid residues 360-416) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 1 (TSR1) or SEQ ID NO: 2 (TSR1(R413Q)). The R413Q mutation has previously been shown to abolish the ability of 3TSR to activate transforming growth factor β (TGFβ), which may promote metastasis, while not affecting the ability of 3TSR to inhibit angiogenesis (Miao et al. *Cancer Res.* 61: 7830-7839, 2001). In other embodiments, the TSR domain, or portion thereof, of human TSP-1 includes the second type 1 repeat (TSR2) of TSP-1 (amino acid residues 417-473) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 3 (TSR2+RFK) or SEQ ID NO: 4 (TSR2). The TSR2+RFK polypeptide includes both TSR2 and the TGFβ activating sequence (RFK). In other embodiments, the TSR domain, or portion thereof, of human TSP-1 includes the third type 1 repeat (TSR3) of TSP-1 (amino acid residues 474-530) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 5 (TSR3). Optionally, the TSR domain, or portion thereof, of human TSP-1 may include all three TSRs (TSR1, TSR2, and TSR3) of TSP-1 (amino acids 360-530) including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 6 (3TSR (R413Q)) or SEQ ID NO: 7 (3TSR). Alternatively, the TSR domain, or portion thereof, of human TSP-1 may include a combination of two different TSRs (e.g., TSR1 and TSR2; TSR2 and TSR3; or TSR1 and TSR3). In some embodiments, the amino acid sequence of the TSR domain, or portion thereof, of human TSP-1 consists of any one of SEQ ID NOs: 1-7.

The TSP-1 polypeptides of the invention may include an Fc region, which may include a CH2 domain and a CH3 domain. The Fc region may further include a hinge region. The CH2 domain and the CH3 domain may be heavy chain constant domains of an immunoglobulin selected from the group consisting of IgG1, IgG2, IgG3, and IgG4. For example, CH2 domain and the CH3 domain may be heavy chain constant domains of immunoglobulin IgG1. Optionally, the Fc region has been engineered to have greater half-life in circulation, which can be achieved, for example, by mutation (e.g., a substitution) of one or more amino acids of the Fc region. For example, the Fc region may include a M252Y/S254T/T256E (YTE) mutation, which has been demonstrated to increase the half-life of therapeutic antibodies in circulation (Dall'Acqua et al. *J. Biol. Chem.* 281: 23514-23524, 2006). YTE mutant IgG has a 10-fold higher affinity for FcRn, a receptor that mediates IgG salvage in endothelial cells. As a result, YTE mutant IgG has a 4-fold longer half-life in circulation, as compared to wild-type IgG, and may have well over a 500-fold longer half-life than recombinant TSR-containing proteins (Dall'Acqua et al. *J. Biol. Chem.* 281: 23514-23524, 2006; U.S. Pat. No. 7,223, 731) or TSR-mimicking peptides, such as ABT-510 and ABT-898 (Abbott Laboratories; Westphal. *Curr. Opin. Mol. Ther.* 6: 451-457, 2004; Greenaway et al. *Mol. Cancer Ther.* 8(1): 64-74, 2009) or CVX-045 (CovX Research; Li et al. *Transl. Oncol.* 4: 249-257, 2011). Accordingly, the Fc region may include an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO: 8, which is an IgG1 polypeptide including the YTE mutation described above. Optionally, the amino acid sequence of the Fc region may include SEQ ID NO: 8 or consist of SEQ ID NO: 8.

The TSP-1 polypeptides of the invention may include the TSP-1 domain and Fc region positioned relative to each other in an N-terminal to C-terminal direction as follows: X-TSP-1 domain-Y-Fc region-Z. Alternatively, the TSP-1 domain and Fc region are positioned relative to each other in an N-terminal to C-terminal direction as follows: X-Fc region-Y-TSP-1 domain-Z. In either of the two above embodiments, each of X, Y, and Z is absent or is an amino acid sequence of at least one amino acid (e.g., at least 2, 3, 4, 5, 6, 7, 8, 9, 10, 15, 20, 25, 30, 35, 40, 45, or 50 or more amino acids). The polypeptide may further include a linker or spacer region positioned between the TSP-1 domain and the Fc region (e.g., when Y is at least one amino acid).

The invention also features TSP-1 polypeptides that include a TSP-1 domain, or portion thereof (e.g., TSP-1 polypeptides that are not fused to an Fc region). These TSP-1 polypeptides may include an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 1-7. In some embodiments, the TSP-1 polypeptide is not full-length thrombospondin-1 (TSP-1). In some embodiments, the TSP-1 polypeptides consist of any one of SEQ ID NOs: 1-7.

As noted above, the invention features polypeptide variants having less than 100% amino acid sequence identity to the polypeptides described herein by amino acid sequence. The variants polypeptides have a lower degree of sequence identity (e.g., less than 100% sequence identity, e.g., 90%, 91%, 92%, 93%, 94%, 95%, 96%, 97%, 98%, or 99% sequence identity) but have sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr and Trp. Guidance concerning which amino acid changes are likely to be phenotypically silent is found in Bowie et al. (*Science.* 247: 1306-1310, 1990) and Table 1 below.

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Optionally, the Fc region is conjugated to a functional moiety (e.g., a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate)). Therefore, the TSP-1 polypeptide of the invention (e.g., 3TSR-Fc fusion protein) may include a cytotoxic agent that acts additively or synergistically with the TSP-1 polypeptide component, e.g., to kill or inhibit tumor cells in the treatment of cancer, e.g., epithelial ovarian cancer (EOC).

Chemotherapeutic agents useful for conjugating to TSP-1 polypeptides of the invention are described. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232, published Oct. 28, 1993. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. (*Science* 238: 1098, 1987). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026). The toxins may effect their cytotoxic and cytostatic effects by mechanisms including tubulin binding, DNA binding, or topoisomerase inhibition.

Alternatively, TSP-1 polypeptides of the invention may be conjugated to one or more small molecule toxins, such as a calicheamicin, maytansinoids, dolastatins, aurostatins, a trichothecene, and CC1065, and the derivatives of these toxins that have toxin activity, are also contemplated herein.

Other anti-tumor agents that can be conjugated to the TSP-1 polypeptides (e.g., 3TSR-Fc fusion proteins) of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

For selective destruction of a tumor, the TSP-1 polypeptides (e.g., 3TSR-Fc fusion proteins) of the invention may comprise a highly radioactive atom. A variety of radioactive isotopes are available for the production of radioconjugated TSP-1 polypeptides. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. *Biochem. Biophys. Res. Commun.* 80:49-57, 1978) can be used to incorporate iodine-123. "Monoclonal Antibodies in Immunoscintigraphy" (Chatal, CRC Press 1989) describes other methods in detail.

Conjugates of the TSP-1 polypeptide and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science.* 238: 1098, 1987. Carbon-14-labeled 1-isothiocyanatobenzyl-3-methyldiethylene triaminepentaacetic acid (MX-DTPA) is an exemplary chelating agent for conjugation of radionucleotide to the TSP-1 polypeptide. See, e.g., WO94/11026.

The TSP-1 polypeptides of the invention expressly contemplate, but are not limited to, conjugates prepared with cross-linker reagents: BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Polynucleotides, Vectors, Host Cells, and Recombinant Methods i. Polynucleotides The invention features polynucleotides encoding one or more (e.g., 1, 2, 3, or 4 or more) of the polypeptides (e.g., TSP-1 fusion and non-fusion proteins, e.g., 3TSR-Fc fusion proteins and 3TSR proteins) of the invention. Polynucleotide sequences encoding one or more polypeptides of the invention can be obtained using standard recombinant techniques. For example, cDNA of a TSP-1 domain, or portion thereof, (e.g., 3TSR) including one or more (e.g., 1, 2, 3, or 4 or more) cloning sites (e.g., an EcoRV cloning site) can be prepared by polymerase chain reaction (PCR).

ii. Vectors

The invention features vectors including one or more (e.g., 1, 2, 3, or 4 or more) of the polynucleotides of the invention. For example, a polynucleotide of the invention may be isolated and inserted into a replicable vector for further cloning (amplification of the DNA) or for expression of the encoded polypeptide. For example, the polynucleotides can be cloned into a pBluescript plasmid and the sequence checked prior to subcloning the DNA into an Fc-encoding plasmid, such as pFUSE-hIgG1-Fc1 (InvivoGen). Many vectors are available. The choice of vector depends in part on the host cell to be used. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al. (U.S. Pat. No. 5,648,237).

In addition, phage vectors containing replicon and control sequences that are compatible with the host microorganism can be used as transforming vectors in connection with these hosts. For example, bacteriophage such as λGEM-11 ™ may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to ligate them to cistrons encoding the target light and heavy chains (Siebenlist et al., *Cell.* 20: 269, 1980) using linkers or adaptors to supply any required restriction sites.

iii. Host Cells

The invention features host cells including one or more vectors of the invention, such as host cells of either prokaryotic origin (e.g., *E. coli* cells) or eukaryotic origin (generally mammalian (e.g., CHO-K1 cells), but also including fungi (e.g., yeast), insect (e.g., *Drosophila* S2 cells), plant, and nucleated cells from other multicellular organisms). In some embodiments, stable clones can be prepared using a conventional selection method, such as Zeocin selection.

a. Prokaryotic Host Cells

Prokaryotic host cells suitable for expressing TSP-1 polypeptides of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, Pseudomonas species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b. Eukaryotic Host Cells

The vector components generally include, but are not limited to, one or more of the following: a signal sequence, an origin of replication, one or more marker genes, an enhancer element, a promoter, and a transcription termination sequence.

A vector of the invention for use in a eukaryotic host cell may contain a signal sequence or other polypeptide having a specific cleavage site at the N-terminus of the mature protein or polypeptide of interest. The heterologous signal sequence selected can be one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the antibody.

Generally, an origin of replication component is not needed for mammalian expression vectors. For example, the SV40 origin may typically be used, but only because it contains the early promoter.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up the TSP-1 nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding a TSP-1 polypeptide, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

Transcription of DNA encoding a polypeptide of the invention (e.g., a 3TSR-Fc fusion protein) by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the TSP-1 polypeptide-encoding sequence, provided that enhancement is achieved, but is generally located at a site 5' from the promoter.

Expression and cloning vectors usually contain a promoter that is recognized by the host organism and is operably linked to the nucleic acid sequence(s) encoding the TSP-1 polypeptide. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors.

Transcription from vectors encoding the TSP-1 polypeptides in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papillomavirus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a TSP-1 polypeptide. One useful transcription termination component is the bovine growth hormone polyadenylation region (see, e.g., WO 94/11026 and the expression vector disclosed therein).

Suitable host cells for cloning or expressing the DNA in the vectors described herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)), e.g., CHO-K1 cells; mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

iv. Recombinant Methods

The invention also features methods of producing one or more of the polypeptides of the invention (3TSR-Fc fusion proteins) whereby host cells (e.g., CHO-K1 cells) can be cultured in a culture medium, and the polypeptides of the invention (e.g., 3TSR-Fc fusion proteins) can be recovered (e.g., purified) from the host cell or culture medium (e.g., conditioned serum-free media using protein-A Sepharose).

The host cells used to produce a polypeptide of this invention (e.g., a 3TSR-Fc fusion protein) may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, hydrophobic interaction columns (HIC), ammonium sulfate precipitation, and gel filtration using, for example, Sephadex G-75.

In one embodiment, as described above, Protein A immobilized on a solid phase is used for immunoaffinity purification of the TSP-1 polypeptides of the invention. Protein A is a 41-kDa cell wall protein from *Staphylococcus aureus* which binds with a high affinity to the Fc region of antibodies (Lindmark et al. *J. Immunol. Meth.* 62:1-13, 1983). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the TSP-1 polypeptide of interest to Protein A. The solid phase is then washed to remove contaminants nonspecifically bound to the solid phase. The TSP-1 polypeptide of interest may be recovered from the solid phase by elution into a solution containing a chaotropic agent or mild detergent. Exemplary chaotropic agents include, but are not limited to, urea, Guanidine-HCl, lithium perchlorate, Histidine, and Arginine. Exemplary mild detergents include, but are not limited to, Tween (e.g., Tween-20), Triton (e.g., Triton X-100), NP-40 (nonylphenoxylpolyethoxylethanol), Nonidet P-40 (octyl phenoxylpolyethoxylethanol), and Sodium Dodecyl Sulfate (SDS). Diluting the TSP-1 polypeptide into a solution containing a chaotropic agent or mild detergent after elution from the column (e.g., mAbSure column) maintains the stability of the TSP-1 polypeptide post-elution.

In another embodiment, a recombinant baculovirus be generated by co-transfecting a vector encoding one or more polypeptides of the invention (e.g., a 3TSR-Fc fusion protein) and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, a TSP-1 polypeptide sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding a TSP-1 polypeptide or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., *Drosophila melanogaster* S2 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged TSP-1 polypeptide can then be purified, for example, by $Ni^{2+}$-chelate affinity chromatography as follows. Extracts can be prepared from recombinant virus-infected S2 cells as described by Rupert et al. (*Nature.* 362: 175-179, 1993). Briefly, S2 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl; 10% glycerol pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TSP-1 polypeptide are pooled and dialyzed against loading buffer.

Purification of the TSP-1 polypeptide can also be performed using known chromatography techniques, including for instance, Protein A or protein G column chromatography. The TSP-1 polypeptide of interest may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available.

Western blotting (e.g., using a polyclonal antibody to the TSRs of TSP-1) may be used to confirm that a protein of the correct molecular weight is produced.

TSP-1 Compositions of the Invention

Any one of the TSP-1 polypeptides (e.g., TSP-1 fusion and non-fusion proteins, e.g., 3TSR-Fc fusion proteins and 3TSR proteins) or polynucleotides encoding the TSP-1 polypeptides of the invention, such as those described above, can be included in compositions (e.g., pharmaceutical compositions). The compositions of the invention may further include a pharmaceutically acceptable carrier, excipient, or diluent. In some embodiments, the compositions may further include an adjuvant.

As described herein, any one of the compositions of the invention may be formulated for treating a disorder associated with pathological angiogenesis (e.g., cancer, e.g., EOC) in a subject (e.g., a human, e.g., a woman).

Epithelial Ovarian Cancer (EOC)

Epithelial ovarian cancer comprises three major histological subtypes: serous, mucinous, and endometrioid. Serous EOC includes serous cystomas, serous benign cystadenomas, serous cystadenomas with proliferating activity of the epithelial cells and nuclear abnormalities but with no infiltrative destructive growth (low potential or borderline malignancy), and serous cystadenocarcinomas. Mucinous EOC includes mucinous cystomas, mucinous benign cystadenomas, mucinous cystadenomas with proliferating activity of the epithelial cells and nuclear abnormalities but with no infiltrative destructive growth (low potential or borderline malignancy), and mucinous cystadenocarcinomas. Endometrioid EOC includes endometrioid tumours (similar to adenocarcinomas in the endometrium), endometrioid benign cysts, endometrioid tumours with proliferating activity of the epithelial cells and nuclear abnormalities but with no infiltrative destructive growth (low malignant potential or borderline malignancy), and endometrioid adenocarcinomas.

In addition, EOC may be categorized by "stages," depending upon how far they have spread beyond the ovary. Thus, Stage I is defined as ovarian cancer that is confined to one or both ovaries. Stage II is defined as ovarian cancer that has spread to pelvic organs (e.g., uterus, fallopian tubes), but has not spread to abdominal organs. Stage III is defined as ovarian cancer that has spread to abdominal organs or the lymphatic system (e.g., pelvic or abdominal lymph nodes, on the liver, on the bowel). Finally, Stage IV is defined as ovarian cancer that has spread to distant sites (e.g., lung, inside the liver, brain, lymph nodes in the neck).

EOCs may also be graded according to the appearance of the cancer cells. Low-grade (or Grade 1) means that the cancer cells look very like the normal cells of the ovary; they usually grow slowly and are less likely to spread. Moderate-grade (or Grade 2) means that the cells look more abnormal than low-grade cells. High-grade (or Grade 3) means that the cells look very abnormal. They are likely to grow more quickly and are more likely to spread.

Signs and symptoms of ovarian cancer are frequently absent early on and when they exist they may be subtle. In most cases, the symptoms persist for several months before being recognized and diagnosed. Most typical symptoms include: bloating, abdominal or pelvic pain, difficulty eating, and possibly urinary symptoms. If these symptoms recently started and occur more than 12 times per month the diagnosis should be considered. Other findings include an abdominal mass, back pain, constipation, tiredness and a range of other non-specific symptoms, as well as more specific symptoms such as abnormal vaginal bleeding or involuntary weight loss. Ascites, or fluid build-up in the abdominal cavity, is also common.

Methods of Treatment of the Invention

The invention features methods of treating a subject (e.g., a human, e.g., a woman) having a disorder associated with pathological angiogenesis (e.g., cancer, e.g., EOC). In one aspect, the invention features methods for the in vivo administration of a therapeutically effective amount of one or more (e.g., 1, 2, or 3 or more) of the compositions of the invention (i.e., polynucleotide or polypeptide compositions of the invention) to treat a subject (e.g., a human, e.g., a woman) having a disorder associated with pathological angiogenesis (e.g., cancer, e.g., EOC). The composition may be administered, for example, such that a dosage of about 0.01 mg/kg/wk to about 10 mg/kg/wk, such as about 0.1 mg/kg/wk to about 1 mg/kg/wk, of the TSP-1 protein (e.g., the 3TSR-Fc fusion protein) is provided.

In another aspect, the invention features methods for the in vivo administration of a therapeutically effective amount of one or more compositions (e.g., 1, 2, or 3 or more) including one or more (e.g., 1, 2, or 3 or more) of a polypeptide including an amino acid sequence having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 1-7 or a polynucleotide encoding the polypeptide. Optionally, the polypeptide is not full-length thrombospondin-1 (TSP-1) and/or the polynucleotide does not encode full-length TSP-1. Optionally, the polypeptide may consist of any one of SEQ ID NOs: 1-7. According to this aspect, the composition may be administered, for example, such that a dosage of about 0.5 mg/kg/day to about 10 mg/kg/day of the TSP-1 protein (e.g., the 3TSR protein) is provided.

In either of the above two aspects, the subject may have EOC, such as Stage III or Stage IV EOC. Accordingly, examples of symptoms of EOC that can be treated using the compositions of the invention include: the size of primary tumors (e.g., a reduction (e.g., by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment) in the size of primary tumors in a subject after administration of the composition to the subject); the presence of metastatic peritoneal tumors and ascites (e.g., a reduction (e.g., by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment) in the presence of metastatic peritoneal tumors and ascites in a subject after administration of the composition to the subject); and/or apoptosis of EOC cells (e.g., induction (e.g., by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment) of apoptosis of EOC cells in a subject after administration of the composition to the subject). These symptoms and/or other symptoms of EOC (see, e.g., above), and their resolution during treatment, may be measured by, for example, a physician during a physical examination or by other tests and methods known in the art. In some embodiments, treatment using one or more of the compositions of the invention may result in a lack of progression of EOC in the subject. In other embodiments, treatment using one or more of the compositions of the invention may result in slowed progression of EOC in the subject relative to common or conventional therapies (e.g., surgery, radiation therapy, chemotherapy, immunotherapy, or hormonal therapy).

Compositions according to the invention described herein may be formulated to release the composition immediately upon administration (e.g., targeted delivery) or at any predetermined time period after administration using controlled or extended release formulations. Administration of the composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastrointestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Optionally, compositions can be formulated, for example, for administration via a localized drug delivery (e.g., a localized slow- or sustained-release drug delivery system). Suitable examples of sustained-release preparations include semipermeable matrices of solid hydrophobic polymers containing the TSP-1 polypeptide (e.g., the 3TSR-Fc fusion protein or 3TSR protein) or polynucleotide encoding the TSP-1 polypeptide, which matrices are in the form of shaped articles, e.g., films, or microcapsule. The microcapsules may be prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated the TSP-1 proteins (e.g., the 3TSR-Fc fusion proteins or 3TSR proteins) of the invention remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Optionally, the compositions can be formulated, for example, for administration via a viral vector (e.g., an adenovirus vector or a poxvirus vector). Recombinant adenoviruses offer several significant advantages for use as vectors for the expression of, for example, one or more of the TSP-1 polypeptides of the invention (e.g., 3TSR-Fc fusion proteins). The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid molecule of the invention) can be prolonged by using cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Acad. Sci. USA* 91:6196 (1994) and Kochanek et al., *Proc. Natl. Acad. Sci. USA* 93:5731 (1996), each herein incorporated by reference).

Adenoviral vectors disclosed in International Patent Application Publications WO 2006/040330 and WO 2007/104792, each incorporated by reference herein, are particularly useful as vectors of the invention. These adenoviral vectors can encode and/or deliver one or more of the TSP-1 polypeptides of the invention (e.g., 3TSR-Fc fusion proteins) to treat a subject having a pathological condition associated with angiogenesis (e.g., cancer, e.g., EOC). In some embodiments, one or more recombinant adenovirus vectors can be administered to the subject in order to express more than one type of TSP-1 polypeptide (e.g., 3TSR-Fc fusion proteins and 3TSR proteins).

Besides adenoviral vectors, other viral vectors and techniques are known in the art that can be used to facilitate delivery and/or expression of one or more of the TSP-1 polypeptides of the invention in a cell or subject (e.g., a human). These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (*Biomed. Pharmacother.* 54:487 (2000), incorporated by reference herein).

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions.

The preferred method of administration can vary depending on various factors (e.g., the components of the composition being administered and the severity of the condition being treated, e.g., Stage I or II EOC compared to Stage III or IV EOC). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the TSP-1 polypeptide (e.g., the 3TSR-Fc fusion protein or 3TSR protein) or polynucleotide encoding the TSP-1 polypeptide of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

The compositions of the invention may be administered after a subject has been diagnosed with a disorder associated with pathological angiogenesis (e.g., cancer, e.g., EOC). The composition may be administered to the subject, for example, 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis. The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject.

When treating a disorder associated with pathological angiogenesis (e.g., cancer, e.g., EOC), the compositions of the invention may be administered to the subject either before the occurrence of symptoms (described hereinabove) or a definitive diagnosis or after diagnosis or symptoms become evident. Accordingly, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of one or more TSP-1 polypeptide (e.g., 3TSR-Fc fusion protein or 3TSR protein) and/or one or more nucleic acids encoding one or more TSP-1 polypeptide (e.g., 3TSR-Fc fusion protein or 3TSR protein), if desired, one or more immunomodulatory agents, such as in a sealed package of tablets or capsules, or in a suitable dry powder inhaler (DPI) capable of administering one or more doses.

i. Dosages

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as epithelial ovarian cells). Additionally, pharmacogenomic (the effect of genotype on the pharmacokinetic, pharmacodynamic, or efficacy profile of a therapeutic) information about a particular patient may affect the dosage used. The composition is preferably administered in an amount that provides a sufficient level of the TSP-1 polypeptide (e.g., 3TSR-Fc fusion protein or 3TSR protein) to yield a therapeutic effect in the subject without undue adverse physiological effects caused by treatment.

The dose of a composition of the invention (e.g., a composition including one or more type of TSP-1 polypeptide or polynucleotide) or the number of treatments using a composition of the invention may be increased or decreased based on the severity of, occurrence of, or progression of, the disorder associated with pathological angiogenesis (e.g., cancer, e.g., EOC) in the subject (e.g., based on the severity of one or more symptoms of EOC described above).

A composition including a TSP-1 polypeptide of the invention (e.g., a TSP-1 fusion protein, e.g., a 3TSR-Fc fusion protein) may be administered, for example, at a dosage of about 0.01 mg/kg/wk to about 10 mg/kg/wk, such as a dosage of about 0.1 mg/kg/wk to about 1 mg/kg/wk, of the fusion protein. Alternatively, a composition including a TSP-1 polypeptide without a fused Fc region may be administered, for example, at a dosage of about 0.5 mg/kg/day to about 10 mg/kg/day of the TSP-1 protein (e.g., the 3TSR protein).

In addition, single or multiple administrations of the compositions of the present invention may be given (pre- or post-diagnosis) to a subject (e.g., one administration or administration two or more times). For example, subjects who are particularly susceptible to, for example, cancer metastasis (e.g., subjects with Stage III or Stage IV EOC) may require multiple treatments to establish and/or maintain a therapeutic effect. For the treatment of a subject having EOC (e.g., Stage III or Stage IV EOC), the efficacy of treatment provided by the pharmaceutical compositions described herein can be monitored by, for example, monitoring and/or measuring primary tumor size, metastatic peritoneal tumors and ascites, and/or apoptosis of EOC cells, whereby a reduction or decrease in primary tumor size and/or metastatic peritoneal tumors and ascites and/or an induction or increase in apoptosis of EOC cells in indicative of effective treatment. The dosages may then be adjusted or repeated as necessary to trigger the desired level of response.

Alternatively, as applies to recombinant therapy, the efficacy of treatment can be determined by monitoring the level of the one or more TSP-1 proteins expressed by or present in a subject (e.g., a human) following administration of the compositions of the invention. For example, the blood or lymph of a subject can be tested for the TSP-1 polypeptide(s) using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of one or more of the compositions of the invention may achieve a therapeutic effect pre-diagnosis. In addition, a single dose administered post-diagnosis can function as a treatment according to the present invention.

A single dose of one or more of the compositions of the invention can also be used to achieve therapy in subjects being treated for a disease (e.g., EOC). Multiple doses (e.g., 2, 3, 4, 5, or more doses) can also be administered, in necessary, to these subjects.

ii. Carriers, Excipients, Diluents

Therapeutic formulations of the compositions of the invention may be prepared using standard methods known in the art by mixing the active ingredient having the desired degree of purity with optional physiologically acceptable carriers, excipients, or stabilizers (Remington's Pharmaceutical Sciences (20$^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

iii. Adjuvants

Any one of the compositions of the invention can be formulated to include, be administered concurrently with, and/or be administered in series with one or more pharmaceutically acceptable adjuvants to increase the immunogenicity of the composition (e.g., upon administration to a subject in need thereof, e.g., a subject having a disorder associated with pathological angiogenesis, e.g., cancer, e.g., EOC). Adjuvants approved for human use include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)] ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

iv. Ex Vivo Transfection and Transduction

The present invention also provides for the ex vivo transfection or transduction of cells, followed by administration of these cells back into a subject (e.g., human) to allow for the expression of one or more of the TSP-1 polypeptides (e.g., 3TSR-Fc fusion proteins) of the invention. In one embodiment, the cells are autologous to the treated subject. Cells can be transfected or transduced ex vivo with, for example, one or more vectors of the invention to allow for the temporal or permanent expression of one or more of the TSP-1 polypeptides (e.g., 3TSR-Fc fusion proteins) in the treated subject. Upon administering these modified cells to the subject, the one or more TSP-1 polypeptides (e.g., 3TSR-Fc fusion proteins) will be expressed, eliciting protective or therapeutic responses.

Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector. Totipotent, pluripotent, multipotent, or unipotent stem cells, including bone marrow progenitor cells and hematopoietic stem cells (HSC), can be isolated and transfected or transduced and administered to a subject in need of treatment.

Kits

The invention provides kits that include a composition of the invention (e.g., a composition including a TSP-1 polypeptide or polynucleotide of the invention). The kits include instructions to allow a clinician (e.g., a physician or nurse) to administer the composition contained therein to a subject to treat a disorder associated with pathological angiogenesis (e.g., cancer, e.g., EOC).

Preferably, the kits include multiple packages of the single-dose pharmaceutical composition(s) containing an effective amount of a polypeptide or polynucleotide of the invention. Optionally, instruments or devices necessary for administering the pharmaceutical composition(s) may be included in the kits. For instance, a kit of this invention may provide one or more pre-filled syringes containing an effective amount of a vaccine, vector, stabilized trimer, or optimized viral polypeptide of the invention. Furthermore, the kits may also include additional components such as instructions regarding administration schedules for a subject having a disorder associated with pathological angiogenesis (e.g., cancer, e.g., EOC) to use the pharmaceutical composition(s) containing a TSP-1 polypeptide or polynucleotide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The present invention is illustrated by the following examples, which are in no way intended to be limiting of the invention.

Example 1. Materials and Methods

Mouse Model of Epithelial Ovarian Cancer (EOC)

All animals were housed and treated in accordance with the Canadian Council on Animal Care. Tumor induction was done as described previously (Greenaway et al. *Gynecol. Oncol.* 121: 532-545, 2007; Greenaway et al. *Mol. Cancer Ther.* 8: 64-74, 2009). Briefly, $10^6$ spontaneously transformed mouse epithelial cells (ID8) were suspended in 5 μL PBS and orthotopically injected under the ovarian bursa of anesthetized syngeneic C57BL/6 mice using a Hamilton syringe (Fisher) and a 30-gauge needle. The contralateral ovary received an injection of 5 μL PBS under the ovarian bursa. Mice were then divided into treatment groups (e.g., 3TSR treatment or control treatment groups).

In this mouse model of EOC, mice develop a distinct primary ovarian tumor by approximately 60 days post tumor induction (PTI), which replicates Stage II EOC in women. By 80 days, mice exhibit signs similar to women with Stage III EOC, with dissemination of small tumors throughout the peritoneum and the beginnings of ascites formation. This is the stage at which the majority of women is diagnosed with EOC and is characterized by a low 5-year survival. By 90 days PTI, mice have large ovarian tumors, widespread peritoneal disease, and abdominal distention due to ascites accumulation (Greenaway et al. *Gynecol Oncol.* 108: 385-394, 2008).

Apoptosis Detection

In vitro, apoptosis was evaluated in ID8 cells following culturing in the presence or absence of 3TSR (3 μM) for 24 hours. Following treatment, cells were fixed in 10% neutral buffered formalin for 1 hour at room temperature and then permeabilized in 0.1% Triton X-100 (Sigma) in PBS. Detection of apoptotic cells was done with a terminal deoxynucleotidyl transferase-mediated dUTP nick end labeling (TUNEL) kit (Roche Applied Sciences) according to the manufacturer's protocol. Following deparaffinization and rehydration, tissue sections were washed in PBS and incubated with the FITC-conjugated TUNEL enzyme for 60 minutes to detect DNA fragmentation. Incubation for 60 minutes with an anti-fluorescein antibody conjugated to a peroxidase to detect incorporated fluorescein. Apoptotic cells were visualized by brief incubation with diaminobenzidine tetrahydrochloride and sections were counterstained by hematoxylin and mounted with Permount. Following TUNEL detection, cells were counterstained with 4',6-diamidino-2-phenylindole and TUNEL-positive and TUNEL-negative cells were counted and expressed as percent apoptotic. In some embodiments, apoptosis can be evaluated in CAOV3, OVCAR-3 and SKOV-3 ovarian cancer cell lines and normal human surface epithelial primary cells. Apoptosis can be additionally quantified by fluorescence-activated cell sorting (FACS) of treated cells as previously described (Ren et al. *Cancer Res.* 69: 3856-3865, 2009).

Collection of Ascites Fluid and Scoring of Secondary Peritoneal Lesions

At euthanasia, mice were positioned in dorsal recumbency and a 25-gauge needle attached to a 10 mL syringe was introduced into the peritoneal space, and the ascites fluid was aspirated. After initial aspiration, a vertical incision was made in the abdomen and any residual ascites fluid not recovered at the initial aspiration was collected. Ascites fluid was transferred to either 10 or 20 mL graduated cylinder for measurement of volume. Tumor dissemination was scored by the number of visible metastasis present within the abdominal cavity. Abdomens with no visible secondary tumors were scored a 0. Presence of one or two secondary lesions scored a 1. Three to 10 secondary lesions were scored 2. Presence of >10 lesions throughout the abdomen received a score of 3.

Western Blots

VEGF and Fas ligand (FasL) protein expression was detected and analyzed in ID8 cells treated with 3TSR by immunoblot analysis. Whole cell lysates of ID8 cells were generated by immersion of cells in liquid nitrogen followed by homogenization in cold lysis buffer. Total protein lysates (10 μg) were separated by SDS-PAGE on 12% gels. Proteins were blotted onto polyvinylidene difluoride (Millipore) membranes then blocked 1 hour at room temperature in 5% (w/v) skim milk. Primary antisera (VEGF, 1:500 (Santa Cruz Biotechnology); FasL, 1:600 (Pharmingen)) were applied overnight at 4° C. on a rocking platform. Blots were washed in TBS-1% Tween 20 and incubated with the appropriate peroxidase-conjugated secondary antibody for 1 hour at room temperature. Reactive protein was detected with enhanced chemiluminescence (Boehringer Mannheim) and Konica medical X-ray film.

Example 2. 3TSR is a Potent Inhibitor of Epithelial Ovarian Cancer (EOC) Growth In Vitro We have found that treatment of murine ovarian surface epithelial (ID8) cells with 3 μM 3TSR in vitro results in a 10-fold increase in apoptosis and a 5-fold decrease in proliferation. ID8 cells were cultured in presence or absence of 3TSR (3 μM) for 24 hours. As depicted in FIG. 1, 3TSR significantly ($p<0.05$) decreased the number of Ki67-positive proliferating cells (open bars) and increased the number of TUNEL-positive apoptotic cells (solid bars). This treatment also increased Fas ligand (FasL) expression and decreased VEGF expression by the tumor cells (FIG. 2A). Daily injection of 3TSR (4 mg/kg/day) inhibits orthotopic ID8 tumor growth by 75% when it is administered for 90 days after tumor cell injection. 3TSR treatment resulted in a decrease in vessel size and density with a selective loss of vessels that lacked pericyte coverage. The effectiveness of the TSR-based approach may be due to the fact that the tumor cells express CD36. Expression of CD36 in the murine ID8 cell line is comparable to that of human dermal microvascular endothelial cells (HDMECs) (FIG. 2B, compare the expression of CD36 from whole cell lysates of HDMEC (lane 1) with ID8 (lane 2)). This observation is consistent with the results of Tetu and co-workers who detected CD36 expression in ovarian cancer tissue by immunohistochemistry (*Mod. Pathol.* 21: 1002-1010, 2008). In addition, CD36 is expressed in EOC cells isolated from patient ascites (R. Watnick and R. Drapkin, personal communication).

Example 3. 3TSR is a Potent Inhibitor of Epithelial Ovarian Cancer (EOC) Growth In Vivo We have recently found that 3TSR is particularly active in an orthotopic model of epithelial ovarian cancer (EOC). When 3TSR was used as a single agent and treatment was initiated at advanced stages of disease, mice showed tumor regression and greatly increased survival.

Figure 3:
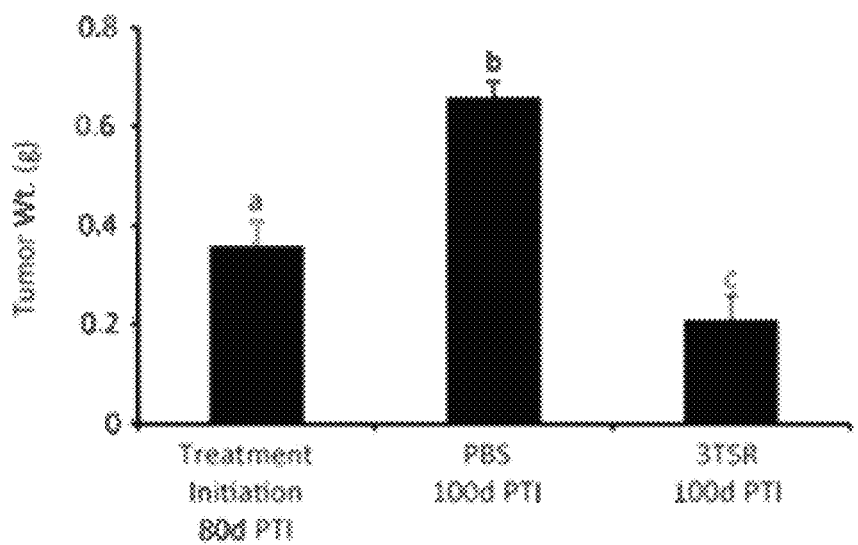
FIG. 3 is a graph showing that 3TSR treatment reduces primary tumor weight and induces regression of advanced stage EOC. At 80 days post tumor induction (PTI), mice were either sacrificed or treated with PBS or 3TSR (4 mg/kg/day) for 20 days. Bars with different letters are statistically different ($p<0.05$).
Figure 4:
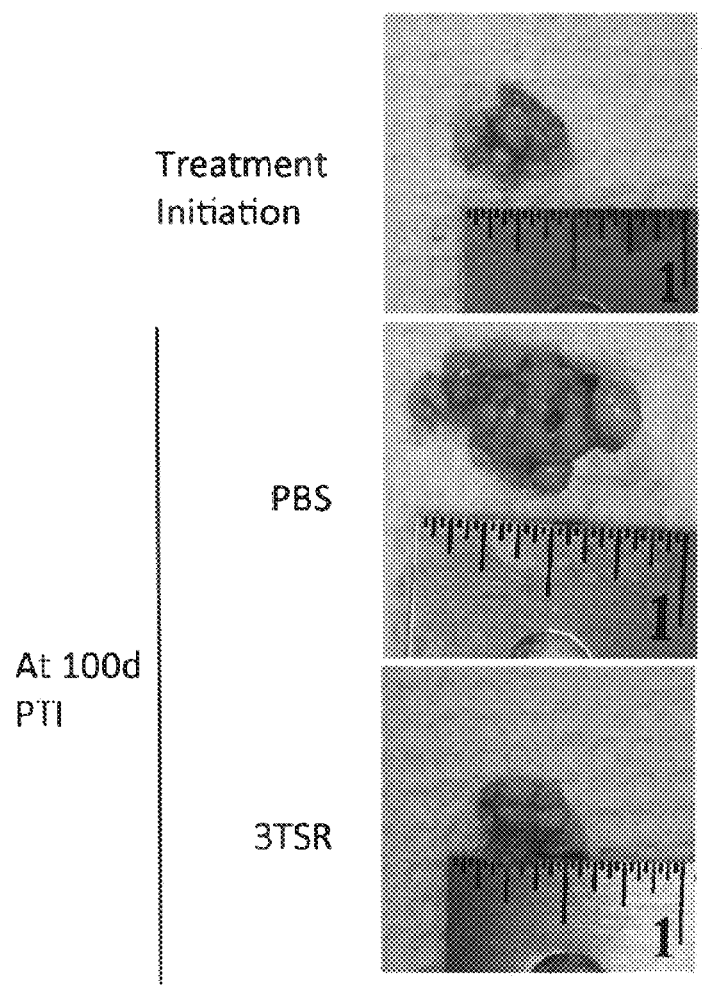
FIG. 4 is a set of images showing that treatment 3TSR reduces primary tumor size and induces regression of advanced stage EOC. Primary tumor at 80 days PTI (top); primary tumor at 100 days PTI with PBS (control) treatment; primary tumor at 100 days PTI with 3TSR (4 mg/kg/day) treatment.

In an intervention trial with the orthotopic model, ovarian tumors were allowed to develop untreated for 80 days post tumor induction (PTI), at which time the mice have large primary tumors, numerous peritoneal metastases and the beginning of hemorrhagic ascites. Treatment with 3TSR for 20 days, as a single agent, induced significant ($p<0.5$) regression of advanced stage EOC compared to control treatment with PBS by reducing primary tumor weight (FIG. 3) and size (FIG. 4) as well as completely eradicating metastatic peritoneal tumors and ascites, which account for the majority of morbidity and mortality associated with EOC.

Along with induction of tumor cell apoptosis and tumor regression, 3TSR normalized the tumor vasculature through specific induction of apoptosis in immature tumor vessels.

Figure 5:
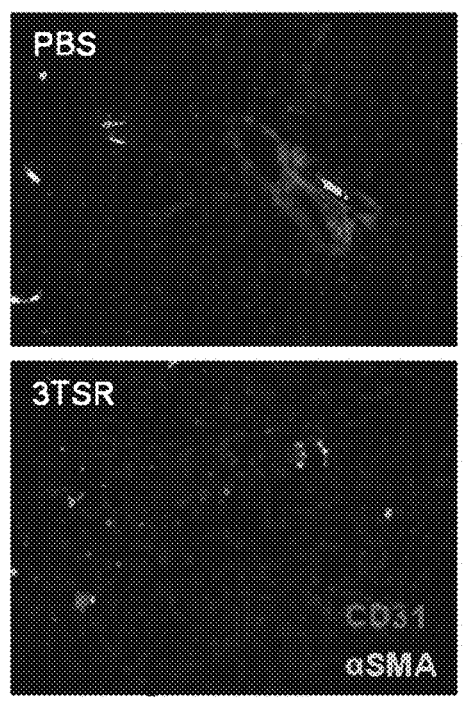
FIG. 5 is a set of immunofluorescence images showing that 3TSR treatment (4 mg/kg/day for 20 days; bottom) of mice at 80 days PTI results in decreases in the size and number of blood vessels and increases in pericyte coverage compared to PBS (control) treatment (top). Endothelial cells were probed for CD31 (red) and pericytes were probed for α-smooth muscle actin (αSMA; green).
Figure 6:
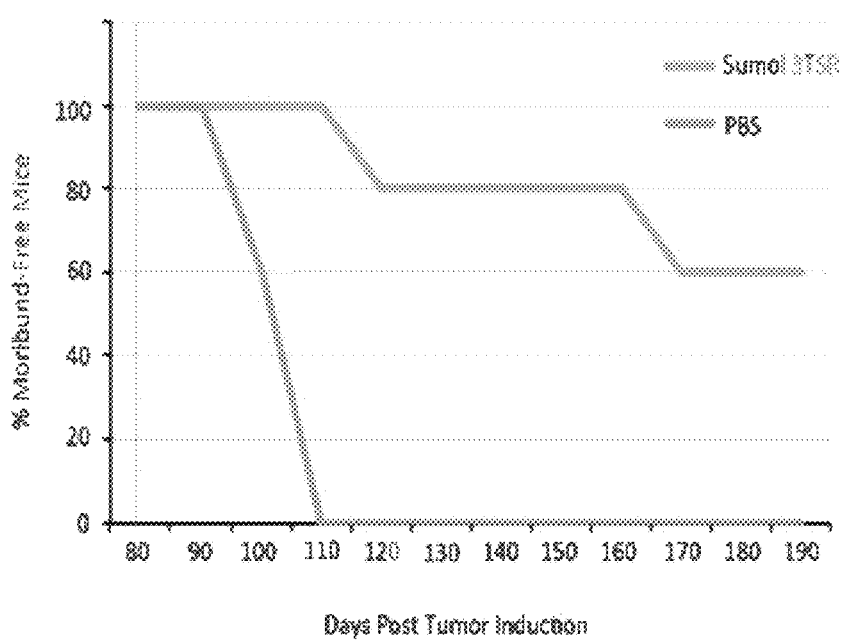
FIG. 6 is a graph showing that 3TSR treatment prolongs survival in a mouse model of EOC. Ovarian tumors were initiated and allowed to develop for 80 days without intervention. At 80 days PTI, mice were either treated with 200 μl PBS (red line) or 3TSR (4 mg/kg/day) in PBS intraperitoneally daily (blue line). Mice were considered moribund when they developed abdominal distention due to ascites.

As depicted in FIG. 5, co-localization immunofluorescence for endothelial cells (CD31, red) and pericytes (αSMA, green) revealed decreases in the size and number of blood vessels and increases in pericyte coverage after 3TSR treatment (bottom) compared to control (PBS) treatment (top). In addition, treatment with 3TSR significantly prolonged survival, with 60% of animals showing no signs of morbidity at 200 days PTI, compared to the loss of all control animals by 110 days (FIG. 6). These data indicate that 3TSR has significant therapeutic potential for the treatment of EOC.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A method of treating a subject having an ovarian cancer, the method comprising administering to the subject a polypeptide comprising a thrombospondin-1 (TSP-1) domain, wherein the TSP-1 domain comprises a 3 TSP-1 repeat (3TSR) domain, at a dosage of about 0.01 mg/kg/wk to about 3.5 mg/kg/wk, thereby reducing the presence of metastatic peritoneal tumors and ascites in the subject.

2. The method of claim 1, wherein the dosage is about 0.01 mg/kg/wk to about 1 mg/kg/wk.

3. The method of claim 2, wherein the reduction in the presence of metastatic peritoneal tumors and ascites in the subject is a reduction of 75% or more in the volume of metastatic peritoneal tumors and ascites compared to prior to administration of the polypeptide.

4. The method of claim 3, wherein the reduction in the presence of metastatic peritoneal tumors and ascites in the subject is a reduction of 99% or more in the volume of metastatic peritoneal tumors and ascites compared to prior to administration of the polypeptide.

5. The method of claim 1, wherein the polypeptide is administered to the subject immediately after diagnosis of the ovarian cancer or clinical recognition of metastatic peritoneal tumors and ascites.

6. The method of claim 1, wherein at least one dose of the polypeptide is administered to the subject.

7. The method of claim 1, wherein the ovarian cancer is an epithelial ovarian cancer (EOC).

8. The method of claim 7, wherein the EOC is a Stage III EOC.

9. The method of claim 7, wherein the EOC is a Stage IV EOC.

10. The method of claim 1, wherein the 3TSR domain comprises an amino acid sequence having at least 90% sequence identity to SEQ ID NO: 7.

11. The method of claim 1, wherein the polypeptide is administered intravenously, subcutaneously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions.

12. The method of claim 2, wherein the dosage is about 0.01 mg/kg/wk to about 0.1 mg/kg/wk.

13. The method of claim 1, wherein the polypeptide further comprises a fragment crystallizable (Fc) region.

14. The method of claim 13, wherein the Fc region comprises a CH2 domain and a CH3 domain.

15. The method of claim 14, wherein the CH2 domain and the CH3 domain are heavy chain constant domains of an immunoglobulin selected from the group consisting of IgG1, IgG2, IgG3, and IgG4.

16. The method of claim 13, wherein the TSP-1 domain and the Fc region are positioned relative to each other in an N-terminal to C-terminal direction as follows: X-TSP-1 domain-Y-Fc region-Z, wherein each of X, Y, and Z is absent or is an amino acid sequence of at least one amino acid.

17. The method of claim 13, wherein the TSP-1 domain and the Fc region are positioned relative to each other in an N-terminal to C-terminal direction as follows: X-Fc region-Y-TSP-1 domain-Z, wherein each of X, Y, and Z is absent or is an amino acid sequence of at least one amino acid.

18. The method of claim 13, wherein the Fc region is conjugated to a functional moiety.

19. The method of claim 18, wherein the functional moiety is a dye, a chemotherapeutic agent, a drug, a growth inhibitory agent, a toxin, or a radioactive isotope.

20. The method of claim 10, wherein the 3TSR domain comprises the amino acid sequence of SEQ ID NO: 7.

21. The method of claim 1, wherein the reduction in the presence of metastatic peritoneal tumors and ascites in the subject is a reduction of 75% or more in the volume of metastatic peritoneal tumors and ascites compared to prior to administration of the polypeptide.

22. The method of claim 1, wherein the polypeptide is administered once per week.

23. The method of claim 1, wherein the polypeptide is administered twice per week.

24. The method of claim 1, wherein the polypeptide is administered continuously.

* * * * *

SEQUENCE LISTING

```
<160> NUMBER OF SEQ ID NOS: 8

<210> SEQ ID NO 1
<211> LENGTH: 57
<212> TYPE: PRT
<213> ORGANISM: Artificial Sequence
<220> FEATURE:
<223> OTHER INFORMATION: Synthetic Construct

<400> SEQUENCE: 1

Ala Asp Asp Gly Trp Ser Pro Trp Ser Glu Trp Thr Ser Cys Ser Thr
1               5                   10                  15

Ser Cys Gly Asn Gly Ile Gln Gln Arg Gly Arg Ser Cys Asp Ser Leu
            20                  25                  30

Asn Asn Arg Cys Glu Gly Ser Ser Val Gln Thr Arg Thr Cys His Ile
        35                  40                  45

Gln Glu Cys Asp Lys Arg Phe Lys Gln
    50                  55

<210> SEQ ID NO 2
<211> LENGTH: 57
<212> TYPE: PRT
<213> ORGANISM: Artificial Sequence
<220> FEATURE:
<223> OTHER INFORMATION: Synthetic Construct

<400> SEQUENCE: 2

Ala Asp Asp Gly Trp Ser Pro Trp Ser Glu Trp Thr Ser Cys Ser Thr
1               5                   10                  15

Ser Cys Gly Asn Gly Ile Gln Gln Arg Gly Arg Ser Cys Asp Ser Leu
            20                  25                  30

Asn Asn Arg Cys Glu Gly Ser Ser Val Gln Thr Arg Thr Cys His Ile
        35                  40                  45

Gln Glu Cys Asp Lys Gln Phe Lys Gln
```

50              55

<210> SEQ ID NO 3
<211> LENGTH: 63
<212> TYPE: PRT
<213> ORGANISM: Artificial Sequence
<220> FEATURE:
<223> OTHER INFORMATION: Synthetic Construct

<400> SEQUENCE: 3

Asp Lys Arg Phe Lys Gln Asp Gly Gly Trp Ser His Trp Ser Pro Trp
1               5                   10                  15

Ser Ser Cys Ser Val Thr Cys Gly Asp Gly Val Ile Thr Arg Ile Arg
            20                  25                  30

Leu Cys Asn Ser Pro Ser Pro Gln Met Asn Gly Lys Pro Cys Glu Gly
        35                  40                  45

Glu Ala Arg Glu Thr Lys Ala Cys Lys Lys Asp Ala Cys Pro Ile
    50                  55                  60

<210> SEQ ID NO 4
<211> LENGTH: 57
<212> TYPE: PRT
<213> ORGANISM: Artificial Sequence
<220> FEATURE:
<223> OTHER INFORMATION: Synthetic Construct

<400> SEQUENCE: 4

Asp Gly Gly Trp Ser His Trp Ser Pro Trp Ser Ser Cys Ser Val Thr
1               5                   10                  15

Cys Gly Asp Gly Val Ile Thr Arg Ile Arg Leu Cys Asn Ser Pro Ser
            20                  25                  30

Pro Gln Met Asn Gly Lys Pro Cys Glu Gly Glu Ala Arg Glu Thr Lys
        35                  40                  45

Ala Cys Lys Lys Asp Ala Cys Pro Ile
    50                  55

<210> SEQ ID NO 5
<211> LENGTH: 57
<212> TYPE: PRT
<213> ORGANISM: Artificial Sequence
<220> FEATURE:
<223> OTHER INFORMATION: Synthetic Construct

<400> SEQUENCE: 5

Asn Gly Gly Trp Gly Pro Trp Ser Pro Trp Asp Ile Cys Ser Val Thr
1               5                   10                  15

Cys Gly Gly Gly Val Gln Lys Arg Ser Arg Leu Cys Asn Asn Pro Thr
            20                  25                  30

Pro Gln Phe Gly Gly Lys Asp Cys Val Gly Asp Val Thr Glu Asn Gln
        35                  40                  45

Ile Cys Asn Lys Gln Asp Cys Pro Ile
    50                  55

<210> SEQ ID NO 6
<211> LENGTH: 171
<212> TYPE: PRT
<213> ORGANISM: Artificial Sequence
<220> FEATURE:
<223> OTHER INFORMATION: Synthetic Construct

<400> SEQUENCE: 6

Ala Asp Asp Gly Trp Ser Pro Trp Ser Glu Trp Thr Ser Cys Ser Thr

```
              1               5                  10                 15
            Ser Cys Gly Asn Gly Ile Gln Gln Arg Gly Arg Ser Cys Asp Ser Leu
                            20                 25                 30

Asn Asn Arg Cys Glu Gly Ser Ser Val Gln Thr Arg Thr Cys His Ile
                        35                 40                 45

Gln Glu Cys Asp Lys Gln Phe Lys Gln Asp Gly Gly Trp Ser His Trp
                    50                 55                 60

Ser Pro Trp Ser Ser Cys Ser Val Thr Cys Gly Asp Gly Val Ile Thr
            65                 70                 75                 80

Arg Ile Arg Leu Cys Asn Ser Pro Ser Pro Gln Met Asn Gly Lys Pro
                            85                 90                 95

Cys Glu Gly Glu Ala Arg Glu Thr Lys Ala Cys Lys Lys Asp Ala Cys
                        100                105                110

Pro Ile Asn Gly Gly Trp Gly Pro Trp Ser Pro Trp Asp Ile Cys Ser
                    115                120                125

Val Thr Cys Gly Gly Gly Val Gln Lys Arg Ser Arg Leu Cys Asn Asn
                            130                135                140

Pro Thr Pro Gln Phe Gly Gly Lys Asp Cys Val Gly Asp Val Thr Glu
            145                150                155                160

Asn Gln Ile Cys Asn Lys Gln Asp Cys Pro Ile
                            165                170

<210> SEQ ID NO 7
<211> LENGTH: 171
<212> TYPE: PRT
<213> ORGANISM: Artificial Sequence
<220> FEATURE:
<223> OTHER INFORMATION: Synthetic Construct

<400> SEQUENCE: 7

Ala Asp Asp Gly Trp Ser Pro Trp Ser Glu Trp Thr Ser Cys Ser Thr
1               5                  10                 15

Ser Cys Gly Asn Gly Ile Gln Gln Arg Gly Arg Ser Cys Asp Ser Leu
                20                 25                 30

Asn Asn Arg Cys Glu Gly Ser Ser Val Gln Thr Arg Thr Cys His Ile
            35                 40                 45

Gln Glu Cys Asp Lys Arg Phe Lys Gln Asp Gly Gly Trp Ser His Trp
        50                 55                 60

Ser Pro Trp Ser Ser Cys Ser Val Thr Cys Gly Asp Gly Val Ile Thr
65                 70                 75                 80

Arg Ile Arg Leu Cys Asn Ser Pro Ser Pro Gln Met Asn Gly Lys Pro
                85                 90                 95

Cys Glu Gly Glu Ala Arg Glu Thr Lys Ala Cys Lys Lys Asp Ala Cys
            100                105                110

Pro Ile Asn Gly Gly Trp Gly Pro Trp Ser Pro Trp Asp Ile Cys Ser
        115                120                125

Val Thr Cys Gly Gly Gly Val Gln Lys Arg Ser Arg Leu Cys Asn Asn
                130                135                140

Pro Thr Pro Gln Phe Gly Gly Lys Asp Cys Val Gly Asp Val Thr Glu
145                150                155                160

Asn Gln Ile Cys Asn Lys Gln Asp Cys Pro Ile
                165                170

<210> SEQ ID NO 8
<211> LENGTH: 227
<212> TYPE: PRT
```

<213> ORGANISM: Artificial Sequence
<220> FEATURE:
<223> OTHER INFORMATION: Synthetic Construct

<400> SEQUENCE: 8

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225
```